United States Patent [19]
Barnhorst et al.

[11] Patent Number: 5,907,067
[45] Date of Patent: May 25, 1999

[54] METHOD OF ALKOXYLATING ALCOHOLS

[75] Inventors: Jeffrey A. Barnhorst; A. Frederick Elsasser, Jr., both of Cincinnati, Ohio; C. William Blewett, Fort Mitchell, Ky.

[73] Assignee: Henkel Corporation, Plymouth Meeting, Pa.

[21] Appl. No.: 08/827,896

[22] Filed: Apr. 9, 1997

Related U.S. Application Data

[60] Provisional application No. 60/016,918, May 6, 1996.
[51] Int. Cl.$^6$ .................................................. C07C 43/11
[52] U.S. Cl. ............................................................ 568/618
[58] Field of Search ............................................. 568/618

[56] References Cited

U.S. PATENT DOCUMENTS

| | | | |
|---|---|---|---|
| 3,970,711 | 7/1976 | Reiche et al. | 568/867 |
| 4,210,764 | 7/1980 | Yang et al. | 568/618 |
| 4,282,387 | 8/1981 | Olstowski et al. | 528/76 |
| 4,962,237 | 10/1990 | Laycock | 568/618 |
| 5,292,910 | 3/1994 | Raths et al. | 554/149 |

OTHER PUBLICATIONS

World Patent Index (WPIDS AN 92–383073, 1992).
Sato et al., "Adsorption of Various Anions by Magnesium Aluminum Oxide" Ind. Eng. Chem. Prod. Res., vol. 25, No. 1, 1986, pp. 89, 90, 92.
KW & DHT, "Acid Acceptors with Good Water Resistance for Halogen–Containing Rubber", Technical Data Sheet, Kyowa Chemical Industry Co., Ltd., Takamatsu, Japan.
KW–2000 Group Technical Data, Kyowa Chemical Industry Co., Ltd., Takamatsu, Japan.

*Primary Examiner*—Gary Geist
*Assistant Examiner*—Jafar Parsa
*Attorney, Agent, or Firm*—Wayne C. Jaeschke; John E. Drach; Joanne Mary Fobare Rossi

[57] ABSTRACT

Alkoxylated alcohols containing no insoluble matter which would prevent the spray application of such materials are obtained by reacting an alcohol and epoxide in the presence of a catalytic amount of a calcined hydrotalcite catalyst to form a crude alkoxylated product. The crude product is then passed through silica gel to remove insoluble by-products.

12 Claims, No Drawings

METHOD OF ALKOXYLATING ALCOHOLS

CROSS-REFERENCE TO RELATED APPLICATIONS

This application claims the benefit of earlier filed and copending provisional application serial number 60/016,918 filed on May 6, 1996, the entire contents of which are incorporated herein by reference.

STATEMENT REGARDING FEDERALLY SPONSORED RESEARCH OR DEVELOPMENT

Not Applicable.

BACKGROUND OF THE INVENTION

This invention pertains to the preparation of alkoxylated alcohols. More specifically, this invention relates to an improvement in the reaction of an alkylene oxide and a long chain alcohol in the presence of a calcined hydrotalcite catalyst wherein insoluble by-products formed in the reaction are readily removed.

Alkoxylated alcohols, especially ethoxylated long chain alcohols, have long been known to be useful as surfactants. It has been found that some ethoxylated long chain alcohols are also useful as mosquito control agents. These ethoxylated alcohols are applied as an approximately monomolecular film to a body of water containing immature forms of mosquitos. The presence of the monomolecular film prevents the emergence of the adult from its aquatic breeding site. Ethoxylated isostearyl alcohol has been found to be especially useful as a mosquito control agent. However, attempts to synthesize ethoxylated isostearyl alcohol which is acceptable for spraying onto a body of water have resulted in failure because the ethoxylated isostearyl alcohol was found to be poorly dispersible in water and exhibited an unacceptably high freezing point.

The use of calcined hydrotalcite as an ethoxylation catalyst produced material which is readily dispersed in water and which had an acceptable freezing point. However, the material was found to contain hazy insoluble white matter which clogged spray nozzles when sprayed onto bodies of water for mosquito control. Therefore, a method of eliminating the presence of the nozzle-clogging material was sought. An object of the invention, therefore, is an alkoxylated alcohol made by the alkoxylation of an alcohol in the presence of a calcined hydrotalcite catalyst that does not contain hazy insoluble matter. A further object of the invention is an ethoxylated isostearyl alcohol that contains no hazy insoluble matter which can clog spray nozzles when sprayed onto bodies of water for mosquito control.

BRIEF SUMMARY OF THE INVENTION

It has been surprisingly discovered that alkoxylated alcohols can be prepared having no insoluble matter which would prevent the spray application of such materials by reacting an alcohol and epoxide in the presence of a catalyst effective amount of a calcined hydrotalcite catalyst to form a crude alkoxylated product. The reaction is carried out such that the product is substantially free of material having an average degree of ethoxylation greater than about 2. The crude product is then passed through silica gel to remove insoluble by-products. The process according to the invention produces a uniform product which, when passed through spray nozzles for mosquito control applications, does not clog the nozzles.

BRIEF DESCRIPTION OF THE SEVERAL VIEWS OF THE DRAWING

Not Applicable.

DETAILED DESCRIPTION OF THE INVENTION

Any type of calcined hydrotalcite catalyst normally used for the alkoxylation of alcohols can be used in the process according to the invention. The preferred calcined hydrotalcite catalyst is a particulate solid formed by calcining a solid layered anionic solid particulate catalyst precursor. This solid layered anionic particulate catalyst precursor is comprised of: (a) a metal in the 3+oxidation state comprising aluminum; (b) at least one secondary metal in the 2+oxidation state; (c) oxygen, bonded to aluminum and the secondary metal or metals; and (d) at least one Lowry-Bronsted anionic base. The catalyst has the general formula I

$$[M^{2+}_{1-x}M^{3+}_x(OH)_2]^{x+}[A^{n-}_{x/n} \cdot {}^mH_2O]^{x-} \qquad (I)$$

wherein $M^{2+}$ is $Mg^{2+}$, $Zn^{2+}$, $Ni^{2+}$, $Co^{2+}$, $Cu^{2+}$, or mixtures thereof; $M^{3+}$ is $Al^{3+}$, $Cr^{3+}$, $Fe^{3+}$, or mixtures thereof; A is $CrO_4^-$; $SO_4^{-2}$; $CO_3^{-2}$; $NO_3^-$; $Cl^-$; $ClO_4^-$; an anion of an aliphatic monocarboxylic acid having from 1 to 44 carbon atoms; two anions of an aliphatic monocarboxylic acid having from 1 to 44 carbon atoms; a dianion of an aliphatic dicarboxylic acid having from 4 to 44 carbon atoms and combinations thereof. The preferred catalysts are those wherein $M^{2+}$ is $Mg^{2+}$, $M^{3+}$ is $Al^{3+}$, and $A^{n-}$ is $CO_3^{-2}$. The catalyst can be prepared by the methods described in U.S. Pat. No. 4,962,237, the entire contents of which are incorporated herein by reference. The calcined hydrotalcite catalyst is commercially available, for example, as KW-2000 from Kyowa Chemical Industry Co., Ltd., Japan.

Any epoxide that is known in the art to react with an alcohol to form an alkoxylated product can be used in the process according to the invention. Such epoxides include but are not limited to ethylene oxide, propylene oxide, butylene oxide, and the like. The preferred epoxide is ethylene oxide.

The silica gel which can be used in the process according to the invention is any silica gel that will remove the normally hazy insoluble material, one component of which is one or more polyalkylene glycols (PAG), made as a by-product during the alkoxylation of an alcohol. In the case of an ethoxylation of an alcohol, the polyalkylene glycols formed are polyethylene glycols (PEG). The preferred silica gel is one having a particle size of 15 microns, a surface area of 700 (m²/g), a pH of a 25% aqueous suspension equal to 3.0, and a pore diameter 10 nm, and is commercially available, for example, as BRITESORB® PM-5108 Selective Adsorbent from The PQ Corporation, Specialty Products Division, P.O. Box 840, Valley Forge, Pa. 19482.

In the process according to the invention, an alcohol and a calcined hydrotalcite catalyst are dried at 120° C. and 29 inches Hg of vacuum to remove any water in the product to reduce the amount of PEG formation. The alcohol is reacted with the epoxide at 140–150° C. The reaction is carried out such that the product is substantially free of material having an average degree of ethoxylation greater than about 2. A principle method of controlling the average degree of ethoxylation to be in the range of about 2 is by limiting the mole ratio of epoxide to alcohol to from about 2/1 to about 2.5/1 and by using the catalysts described herein. This also results in a product typically having a decreased amount of polyol, such as a PEG, which is less than about 0.5% by weight as determined by the method set forth in Example 3 below. The alkoxylated product can then be worked up in one of two ways. The first way is to cool the alkoxylated product to 60° C. and then wash it once or twice with an aqueous alkali metal sulfate solution such as $Na_2SO_4$ or $K_2SO_4$, preferably twice with a 5% aqueous solution of $Na_2SO_4$, and then drying the washed product before contacting with 5 wt % silica gel. The second method comprises stirring the alkoxylated product at reaction temperature for 30 minutes and then contacting it with the 5 wt % silica gel without the washing step. In either instance, the product plus silica gel is then pumped through a press to remove the silica gel, catalysts and insoluble by-products of the reaction.

The following examples are meant to illustrate but not to limit the invention.

EXAMPLE 1

One mole of isostearyl alcohol and 0.5 wt % by weight of hydrotalcite catalyst (KW-2000 obtained from Kyowa Chemical Industry Co., Ltd., Japan) were dried at 120° C. and 29 inches Hg of vacuum for 30 minutes. The alcohol was ethoxylated in a pressure reactor at 140–150° C. by adding two moles of ethylene oxide at a rate to keep the reactor pressure below 50 psi. After all the EO was added, the reaction was continued for 1 hour then stripped under 29 inches Hg vacuum to remove any residual EO and any other volatile by-products such as dioxanes. The product was cooled to 60° C. and 5% by weight BRITESORB® PM-5108 was added and stirred for 30 minutes at 60° C. The product plus the BRITESORB® PM-5108 was then pumped through a press to remove the BRITESORB® PM-5108 to yield a clear product free of hazy insoluble material.

EXAMPLE 2

The procedure of Example 1 was followed except that after cooling the crude product to 60° C. it was washed twice with 5% $Na_2SO_4$ and dried before contacting it with BRITESORB® PM-5108 and then pumping through a press to remove the BRITESORB® PM-5108 to yield a clear product free of hazy insoluble material.

EXAMPLE 3

SEMI-QUANTITATIVE DETERMINATION OF FREE POLYETHYLENE GLYCOL IN ETHOXYLATED ISOSTEARYL ALCOHOL

This method determines the free polyethylene glycol (PEG) content in ethoxylated isostearyl alcohol, semi-quantitatively, by thin-layer chromatography (TLC). The free PEG is separated from the ethoxylated isostearol oligomers by normal phase TLC. Visualization is achieved by means of iodine vapor and semi-quantification is performed by visual comparison of sample and standard PEG band intensity and size.

Apparatus: (a) Two glass TLC tanks and lids: inner dimensions 27.5×27.5×7.5 cm, cat. no. Z12,619-5, Supelco, Inc, Supelco Park, Bellefonte, Pa. 16823-0048; (b) One 10 µL syringe, cat. no. 2-1395, Supelco, Inc.; (c) One 10-mL volumetric flask per sample, cat. no. 29502-124, VWR Scientific Products, 1430 Waukegan, Ill. 60085; (d) Three 100 mL volumetric flasks, cat. no. 29619-610, VWR, Scientific Products; (e) Filter paper, 32 cm., cat. no. 28450-229, VWR, Scientific Products; (f) Two 10 mL pipets—cat. no. 53047-126, VWR, Scientific Products.

Reagents:
   a. Chloroform—stabilized with 1% ethanol, cat. no. BJ048-4, VWR Scientific Products.
   b. Iodine—crystals, cat. no. EM-IX0125-2, VWR Scientific Products.
   c. Polyethylene glycol 600—cat. no. 20,240-1, Aldrich Chemical Company, P.O. Box 2060, Milwaukee, Wis. 53201.
   d. Acetone—cat. no. BJ010-4, VWR Scientific Products.
   e. Methanol—cat. no. BJAH230-4, VWR Scientific Products.
   f. Silica gel G thin layer chromatography plates—cat. no. 01011, Analtech, Inc., P.O. Box 7558, 75 Blue Hen Drive, Newark, Del. 19714.
   g. TLC spotting guide, cat. no. 7624, Alltech Associates, 2051 Waukegan, Ill. 60015.

Preparation of Mobile Phase, Standard and Sample Solutions:
   a. Mobile phase: 30:47:23 v/v acetone:chloroform:methanol. Prepared by adding 30 mL of acetone, 47 mL of ethanol, and 23 mL of methanol, separately, into a 100 mL unstoppered graduated cylinder, capping, and thoroughly mixing by shaking for 15 seconds.
   b. Standard polyethylene glycol solutions:
      1. PEG 600
         1a. Prepare 0.500 µg/µL PEG 600 standard solution by weighing 0.0500 g of PEG 600 within 0.0002 g. into a tared 100 mL. volumetric flask, diluting to volume with chloroform, capping, and thoroughly mixing by shaking for 15 seconds.
         1b. Prepare 0.050 µg/µL PEG 600 standard solution by pipetting a 10 mL aliquot of the 0.500 µg/µL PEG 600 standard solution into tared 100 mL. volumetric flask, diluting to volume with chloroform, capping, and thoroughly mixing by shaking for 15 seconds.
         1c. Prepare 0.005 µg/µL PEG 600 standard solution by pipetting a 10 mL aliquot of the 0.050 µg/µL PEG 600 standard solution into tared 100 mL. volumetric flask, diluting to volume with chloroform, capping, and thoroughly mixing by shaking for 15 seconds.

Preparation of TLC Tank and Iodine Tank:
   a. TLC Tank:
      1. Cut a large square of the filter paper and place it vertically into the tank.
      2. Cover the TLC tank with saran wrap and seal with the glass cover.
   b. Iodine Tank:
      1. Cover the bottom of the iodine tank with iodine crystals. Immediately replace the saran wrap and cover.

Procedure:
   1. Using the spotting guide, spot 10 µL of the 0.500, 0.050, and 0.005 µg/µL PEG 600 standard solutions 1 cm. from the bottom of the plate TLC plate.
   2. Using the spotting guide, spot 10 µL of each sample solution 1 cm. from the bottom of the plate TLC plate.
   3. Using the spotting guide draw a line across the top of the plate 15 cm above the starting point and label each spot at the top of the plate along with the date.
   4. Pour the 100 mL of mobile phase over the filter paper and immediately place the spotted TLC plate into the tank and cover it with Saran Wrap and the glass plate.
   5. Allow solvent front to advance to the 15 cm mark, withdraw the plate and place it into a hood to dry for 15 minutes.
   6. Place the dried TLC plate into the iodine chamber, cover and wait for 30 minutes for visualization.

Visualization and Semi-quantification:
1. Compare each sample spot size and intensity to each of the standards' spots.
2. The standard spots are equivalent to 2.5%. 1.25%, and 0.25% w/w based on the sample and standard concentrations and spotting.
3. Limit of Semi-quantification: The limit of semi-quantification for PEG 600 via iodine visualization under the conditions described are 0.25% w/w. which corresponds to 0.5 μg.
4. Report the % w/w PEG to the nearest 0.25%.

What is claimed is:

1. A process for making an alkoxylated alcohol comprising the steps of: (1) reacting an alcohol and epoxide in the presence of a catalyst effective amount of a calcined hydrotalcite catalyst; (2) contacting the product of the reaction of step (1) with silica gel to remove insoluble by-products.

2. The process of claim 1 wherein said alkoxylated alcohol is isostearyl alcohol.

3. The process of claim 1 wherein said epoxide is ethylene oxide.

4. The process of claim 2 wherein the mole ratio of ethylene oxide to isostearyl alcohol is from about 2/1 to about 2.51

5. The process of claim 1 wherein said hydrotalcite catalyst is a solid layered anionic particulate catalyst precursor is comprised of: (a) a metal in the 3+oxidation state comprising aluminum; (b) at least one secondary metal in the 2+oxidation state; (c) oxygen, bonded to aluminum and the secondary metal or metals; and (d) at least one Lowry-Bronsted anionic base.

6. The process of claim 1 wherein said hydrotalcite catalyst is a compound of the formula I

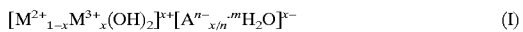

$$[M^{2+}_{1-x}M^{3+}_{x}(OH)_2]^{x+}[A^{n-}_{x/n} \cdot {}^{m}H_2O]^{x-} \qquad (I)$$

wherein $M^{2+}$ is $Mg^{2+}$, $Zn^{2+}$, $Ni^{2+}$, $Co^{2+}$, $Cu^{2+}$, or mixtures thereof; $M^{3+}$ is $Al^{3+}$, $Cr^{3+}$, $Fe^{3+}$, or mixtures thereof; A is $CrO_4^-$; $SO_4^{-2}$; $CO_3^{-2}$; $NO_3^-$; $Cl^-$; $ClO_4^-$; an anion of an aliphatic monocarboxylic acid having from 1 to 44 carbon atoms; two anions of an aliphatic monocarboxylic acid having from 1 to 44 carbon atoms; a dianion of an aliphatic dicarboxylic acid having from 4 to 44 carbon atoms or a combination thereof.

7. The process of claim 1 wherein said silica gel has a particle size of 15 microns, a surface area of 700 (m2/g), the pH of a 25% aqueous suspension equal to 3.0, and a pore diameter 10 nm.

8. A process for making an ethoxylated isostearyl alcohol comprising the steps of: (1) reacting isostearyl alcohol and ethylene oxide in the presence of a catalyst effective amount of a calcined hydrotalcite catalyst the formula I

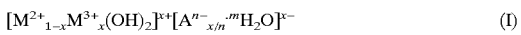

$$[M^{2+}_{1-x}M^{3+}_{x}(OH)_2]^{x+}[A^{n-}_{x/n} \cdot {}^{m}H_2O]^{x-} \qquad (I)$$

wherein $M^{2+}$ is $Mg^{2+}$, $Zn^{2+}$, $Ni^{2+}$, $Co^{2+}$, $Cu^{2+}$, or mixtures thereof; $M^{3+}$ is $Al^{3+}$, $Cr^{3+}$, $Fe^{3-}$, or mixtures thereof, A is $CrO_4^-$; $SO_4^{-2}$; $CO_3^{-2}$; $NO_3^-$; $CL^-$; $ClO_4^-$; an anion of an aliphatic monocarboxylic acid having from 1 to 44 carbon atoms; two anions of an aliphatic monocarboxylic acid having from 1 to 44 carbon atoms; a dianion of an aliphatic dicarboxylic acid having from 4 to 44 carbon atoms or a combination thereof wherein the mole ratio of ethylene oxide to isostearyl alcohol is from about 2/1 to about 2.5/1; (2) contacting the reaction product of step (2) with silica gel to remove insoluble by-products.

9. The process of claim 8, wherein said silica gel has a particle size of 15 microns, a surface area of 700 (m2/g), the pH of a 25% aqueous suspension equal to 3.0, and a pore diameter 10 nm.

10. A process for making an ethoxylated isostearyl alcohol comprising the steps of: (1) reacting isostearyl alcohol and ethylene oxide in the presence of a catalyst effective amount of a calcined hydrotalcite catalyst the formula I

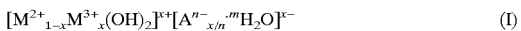

$$[M^{2+}_{1-x}M^{3+}_{x}(OH)_2]^{x+}[A^{n-}_{x/n} \cdot {}^{m}H_2O]^{x-} \qquad (I)$$

wherein $M^{2+}$ is $Mg^{2+}$, $Zn^{2+}$, $Ni^{2+}$, $Co^{2+}$, $Cu^{2+}$, or mixtures thereof; $M^{3+}$ is $Al^{3+}$, $Cr^{3+}$, $Fe^{3+}$, or mixtures thereof; A is $CrO_4^-$; $SO_4^{-2}$; $CO_3^{-2}$; $NO_3^-$; $Cl^{31}$; $ClO_4^-$; an anion of an aliphatic monocarboxylic acid having from 1 to 44 carbon atoms; two anions of an aliphatic monocarboxylic acid having from 1 to 44 carbon atoms; a dianion of an aliphatic dicarboxylic acid having from 4 to 44 carbon atoms or a combination thereof wherein the mole ratio of ethylene oxide to isostearyl alcohol is from about 2/1 to about 2.5/1; (2) washing the product of the reaction of step (1) with an aqueous solution of an alkali metal sulfate and drying the washed product; (3) contacting the dried washed product of step (2) with silica gel to remove insoluble by-products.

11. The process of claim 10 wherein said silica gel has a particle size of 15 microns, a surface area of 700 (m2/g), the pH of a 25% aqueous suspension equal to 3.0, and a pore diameter 10 nm.

12. The process of claim 10 wherein said aqueous solution is a 5% by weight aqueous $Na_2SO_4$ solution.

* * * * *